United States Patent
Moghe et al.

(10) Patent No.: US 7,799,332 B2
(45) Date of Patent: *Sep. 21, 2010

(54) COMPOSITION FOR A CLEAR COSMETIC STICK

(75) Inventors: Bhalchandra Moghe, White House Station, NJ (US); Thomas Schamper, Cranbury, NJ (US)

(73) Assignee: Coty Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/138,180

(22) Filed: May 1, 2002

(65) Prior Publication Data

US 2003/0206931 A1    Nov. 6, 2003

(51) Int. Cl.
*A61K 8/02* (2006.01)
*A61K 8/00* (2006.01)

(52) U.S. Cl. ......................... 424/401; 424/65
(58) Field of Classification Search ............... 424/400, 424/401, 405, 409, 65, DIG. 5
See application file for complete search history.

(56) References Cited

U.S. PATENT DOCUMENTS

| | | | | |
|---|---|---|---|---|
| 4,226,889 A | | 10/1980 | Yuhas | 424/59 |
| 4,268,498 A | * | 5/1981 | Gedeon et al. | 424/59 |
| 4,759,924 A | | 7/1988 | Luebbe et al. | 424/42 |
| 4,948,578 A | * | 8/1990 | Burger et al. | 424/68 |
| 5,316,761 A | * | 5/1994 | Brazinsky | 424/65 |
| 5,407,668 A | * | 4/1995 | Kellner | 424/65 |
| 5,462,736 A | | 10/1995 | Rech et al. | |
| 5,635,164 A | * | 6/1997 | Moghe et al. | 424/65 |
| 6,531,119 B1 | * | 3/2003 | Hall-Puzzio et al. | 424/65 |

FOREIGN PATENT DOCUMENTS

| | | |
|---|---|---|
| EP | 0498488 A2 | 8/1992 |
| WO | WO-9637186 | 11/1996 |
| WO | WO-0195870 A2 | 12/2001 |

OTHER PUBLICATIONS

"U.S. Appl. No. 11/874,043, Restriction Requirement mailed Dec. 30, 2009", 8 pgs.
"Canadian Application Serial No. 2,483,907 Office Action mailed Nov. 4, 2009", 3 pgs.
"European Application Serial No. 09001851.6, Extended European Search Report mailed Apr. 21, 2009" 10 pgs.
"U.S. Appl. No. 11/874,043, Non-Final Office Action mailed Apr. 15, 2010", 10 pgs.
"Canadian Application Serial No. 2,483,907, Response filed May 4, 2010 to Official Action dated Nov. 4, 2009", 8 pgs.
"European Application Serial No. 03747685.0, Brief Communication dated Dec. 10, 2008", 1 pg.
"European Application Serial No. 03747685.0, Communication dated Jul. 21, 2006", 2 pgs.
"European Application Serial No. 03747685.0, Communication dated Dec. 27, 2005", 6 pgs.
"European Application Serial No. 03747685.0 Amendment dated Nov. 11, 2008", 5 pgs.
"European Application Serial No. 03747685.0, Communication under Rule 71(3) dated Jul. 1, 2008", 25 pgs.
"European Application Serial No. 03747685.0, European Search Report dated May 20, 2005", 3 pgs.
"European Application Serial No. 03747685.0, Response filed Jun. 29, 2006 to Communication dated Dec. 27, 2005", 6 pgs.
"International Application Serial No. PCT/US03/22952, International Preliminary Examination Report mailed May 5, 2005", 6 pgs.
"International Application Serial No. PCT/US03/22952, International Search Report mailed Dec. 15, 2003", 6 pgs.
"International Application Serial No. PCT/US03/22952, Written Opinion mailed Jun. 24, 2004", 5 pgs.

* cited by examiner

*Primary Examiner*—Sreeni Padmanabhan
*Assistant Examiner*—Layla Soroush
(74) *Attorney, Agent, or Firm*—Schwegman, Lundberg & Woessner, P.A.

(57) ABSTRACT

The present invention includes a clear cosmetic stick that has a clarity that is stable over a temperature of 5 to 45 degrees Centigrade for a time period of at least about twelve months. The clear cosmetic stick includes one or more of a branched chain fatty acid surfactant and a straight-chain fatty alcohol surfactant.

8 Claims, 4 Drawing Sheets

COMPOSITION FOR A CLEAR COSMETIC STICK

The present invention relates to a clear cosmetic stick and to a method for making a clear cosmetic stick.

BACKGROUND OF THE INVENTION

Clarity and transparency in cosmetic formulations are desired attributes because these features connote freshness, purity, and cleanliness to the cosmetic products. The mass production of clear cosmetic products has been challenging, however, because some of the ingredients employed to promote clarity and transparency have lacked stability when subjected to temperature variations and have lacked stability in storage over time.

Many clear cosmetic formulations have employed soap gel technology. Some of these formulations are described in U.S. Pat. No. 4,759,924 (Luebbe et al). and U.S. Pat. No. 4,226,889 (Yuhas). The reference EP 0 498 488 A2 describes a cosmetic stick with soap partially replaced by polyethylene oxide-polypropylene oxide copolymer. Another formulation with a soap gelling agent is described in WO 96/37186. This formulation describes clarifying agents such as $C_{14-15}$ Pareth 2.25, $C_{14-15}$ Pareth13, Ceteareth-55, PPG-10 cetyl ether, PEG-6 Lauramide, and dimethicone copolymers with ethylene oxide and/or propylene oxide side chains.

Cosmetic sticks generally have a firmness that permits application of a desired amount of active ingredients when the stick is applied over skin. The degree of firmness required depends upon the specific application. The firmness desired has generally been difficult to maintain in transport and storage in environments having high temperatures.

SUMMARY

Figure 1:
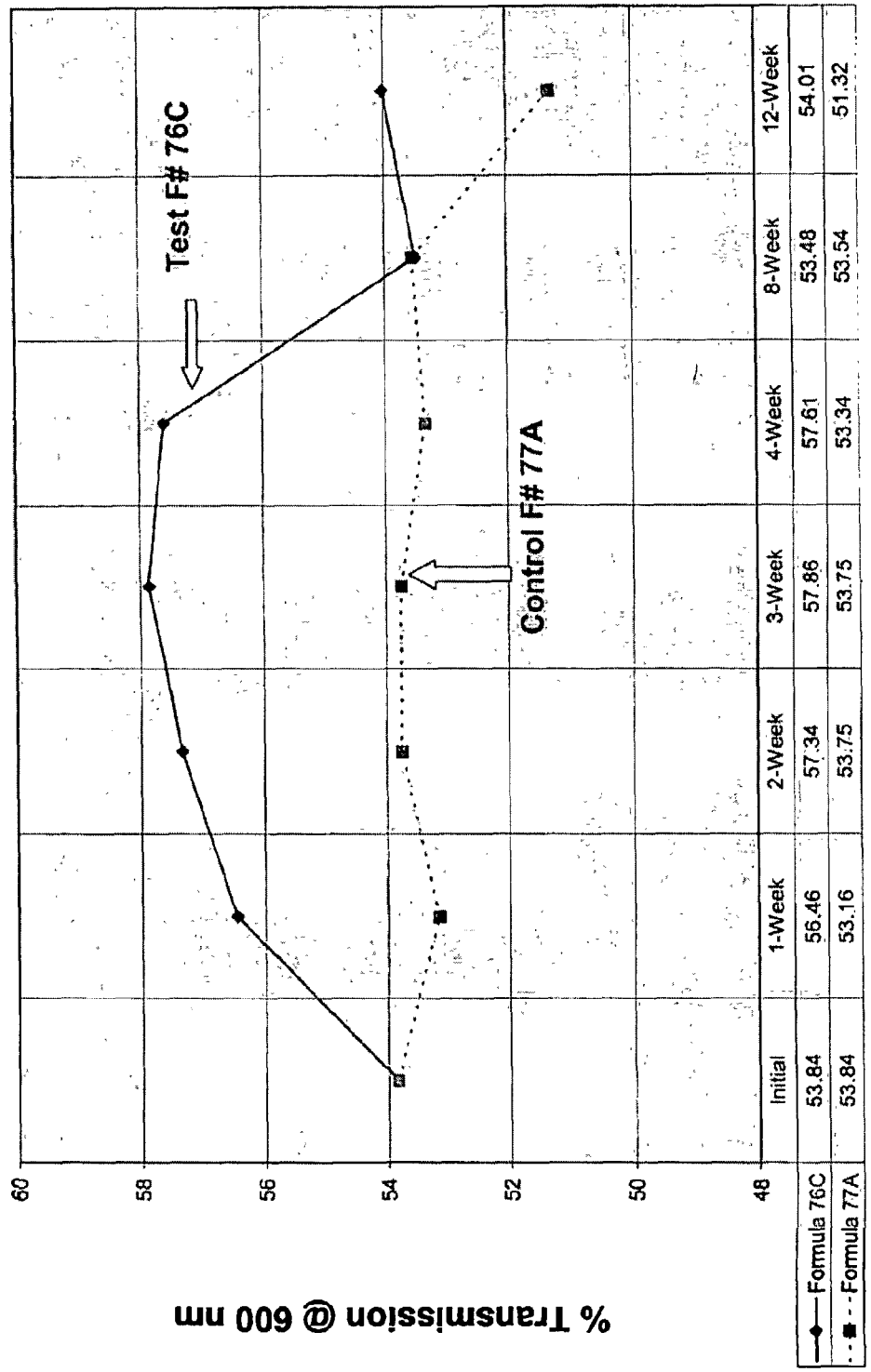
FIG. 1 is a graphical view of one embodiment of the clear cosmetic stick of the present invention and a second cosmetic stick outside of the present invention, stored at ambient temperature for 12 weeks.

One embodiment of the present invention includes a clear cosmetic stick. The clear cosmetic stick includes one or more of a branched chain fatty alcohol surfactant, a straight-chain fatty alcohol surfactant, and a polyhydric alcohol. The branched chain fatty alcohol surfactant and straight-chain fatty alcohol surfactant have concentrations effective for maintaining clarity over a temperature range of 5 to 45 degrees Centigrade for a time period of at least twelve months.

Another embodiment of the present invention includes a clear stick comprising a branched chain fatty alcohol surfactant and a straight chain fatty alcohol surfactant. The two surfactants have concentrations effective for maintaining clarity over a temperature range of 5 to 45 degrees Centigrade for a time period of at least twelve months.

One other embodiment is a method for making a clear cosmetic stick. The method includes providing a polyhydric alcohol and a deodorant active material and mixing the polyhydric alcohol with the deodorant active material together to form a deodorant active mixture. A soap, gel forming agent is added to the deodorant mixture to form a gel-forming mixture. One or more of a branched chain fatty alcohol surfactant and a straight chain fatty alcohol surfactant are added to the gel-forming mixture to impart clarity. The clarity of the mixture is maintained at temperatures of up to 45 degrees Centigrade. Sodium hydroxide is added to the clarified mixture. The clarified mixture is poured into a container to impart a clear stick conformation to the clarified mixture. The clarity of the clear stick is maintained when stored at temperatures of up to 45 degrees Centigrade for at least about twelve months.

Another embodiment of the present invention includes a method for stabilizing clarity in a clear cosmetic stick. The method includes providing ingredients effective for making a clear cosmetic stick. The method also includes preparing a mixture comprising one or more of a branched chain fatty alcohol surfactant and a straight chain fatty alcohol surfactant. The method also includes adding the mixture to the ingredients in a concentration effective to stabilize clarity of the clear cosmetic stick for at least about twelve months at temperatures as high as 45 degrees Centigrade.

One other embodiment includes a clear fragrance stick. The fragrance stick includes one or more of a branched chain fatty acid surfactant, a straight-chain fatty alcohol surfactant, a fragrance oil in a concentration up to 10 percent by weight, and a polyhydric alcohol in a concentration effective for maintaining clarity for a time period of at least about four months.

Another embodiment includes a clear blush stick. The clear blush stick comprises one or more of a branched chain fatty acid surfactant, a straight-chain fatty alcohol surfactant, a color in a concentration of up to 10 percent by weight, and a polyhydric alcohol in a concentration effective for maintaining clarity for a time period of at least about one month.

DETAILED DESCRIPTION

In its product aspect, the present invention includes a clear cosmetic stick having a clarity that is stable over a broad temperature range, from 5 degrees Centigrade to 45 degrees Centigrade, for a period of time in excess of twelve months. The clear cosmetic stick of the present invention has a composition that includes one or more clarifying agents which imparts stable clarity over a broad temperature range, from 5 degrees Centigrade to 45 degrees Centigrade, over an extended period of time. In one embodiment, the period of time for which the clear cosmetic stick is stable exceeds twelve months. In addition to having stability over time, the clear stick is stable when subjected to temperature cycles over a range of ambient temperature to 45 degrees Centigrade.

In one embodiment, the clarity agent is a system that includes Isosteareth-20, which is also known as PEG-20 Isostearyl ether, having an HLB of 15.2 and steareth-2, which is also known as PEG-2 stearyl ether, having an HLB of 4.9. The clarity agent system has, for some embodiments, a concentration of 3.5 to 8.5% by weight of a clear cosmetic stick. The term "HLB" as used herein refers to "hydrophile-lipophile blend."

The clear cosmetic stick of the present invention is resistant to reactions that impair clarity of the stick, such as crystal formation, for a period of time in excess of twelve months. Thus, the clear cosmetic stick of the present invention has a long shelf life. Because of the long shelf life, the clear stick does not have to be immediately purchased by a consumer and does not have to be quickly used by the consumer.

Furthermore, the cosmetic stick of the present invention resists adverse changes in clarity when exposed to temperatures in a range of about 5 to 45 degrees Centigrade. This feature permits the clear cosmetic sticks to be stored under a wide range of elevated temperature conditions and permits the clear cosmetic sticks to be sold in regions having a hot or cold climate.

The composition of the present invention includes a combination of polyethylene glycol (PEG) ethers to give a clear stick. One combination of PEG ethers includes a branched chain fatty alcohol. Another element of the combination of PEG ethers includes a straight-chain fatty alcohol.

One formula composition of the present invention is as follows:

| Ingredient | First Range (%) | Second Range (%) |
|---|---|---|
| Propylene glycol | 45–80 | 65–75 |
| Deionized Water | 5–35 | 12–20 |
| Sodium Stearate | 5–8 | 6–8 |
| Isosteareth-20 | 2.5–8 | 3–7 |
| Steareth-2 | 0–2 | 0.5–1.5 |
| Triclosan | 0.01–0.5 | 0.1–0.2 |
| 10% Sodium Hydroxide | 0–0.3 | 0.10 |
| Fragrance | 0.1–5.0 | 0.5–2.0 |
| Color solution | QS | QS |

The Isosteareth-20 is also known by the tradename IS-20, and is obtained from RTD Chem. The Steareth-2 is also known by tradename Brij-72 and is manufactured by Uniqema of Gouda, The Netherlands.

The term "cosmetic stick", as used herein, refers to a clear stick having use as a deodorant stick, an insect repellant stick, a sunscreen stick, a skin care stick, a cologne stick, a blush stick, and other stick embodiments.

The term "clear", as used herein, has its usual dictionary definition. A clear cosmetic stick allows for ready viewing of objects behind it. Typically, a one centimeter slice of the clear stick of the present invention permits over a 60% transmittance of light of any wavelength in the range of 600-900 nm. Applicants are not bound by this range of transmittance, however, relying on the usual dictionary definition of "clear" and the meaning known in the art.

The clear stick of the present invention is made by combining a polyhydric alcohol solvent, such as propylene glycol and Triclosan to form a deodorant active mixture. The deodorant active mixture is blended while heating to 85-90 degrees Centigrade.

While propylene glycol is described, it is understood that other polyhydric alcohols are suitable for use in the formulation of the present invention. The other polyhydric alcohols include dipropylene glycol, ethylene glycol, trimethylene glycol, glycerol, and sorbitol.

The Triclosan, which is also known as 2-4-4'-trichloro-2'-hydroxyphenyl ether, is a deodorant active material useful as an antibacterial agent. While Triclosan is described, it is believed that other bacteriostats are suitable for use in the clear stick of the present invention. The other bacteriostats include sodium N-lauroyl sarcosine, sodium N-palmitoyl sarcosine, lauroyl sarcosine, N-myristoyl glycine, potassium N-lauroyl sarcosine, and aluminum chlorohydroxy lactate and mixtures of these materials.

Sodium stearate is added to the hot deodorant active mixture and is mixed until the deodorant active mixture is clear and uniform. The gel forming mixture is liquid at 85 to 90 degrees Centigrade. Sodium stearate is a soap, gel-forming agent. Other soap, gel-forming agents suitable for use in the clear stick formulation of the present invention include sodium palmitate, sodium laurate, sodium arachidate, sodium behenate, sodium myristate, and other sodium salts of saturated or unsaturated fatty acids containing from about 10 to 22 carbon atoms. Mixtures of these materials are also suitable. Decisions about the type and concentration of gel-forming agent employed in the clear cosmetic stick of the present invention are made based upon the final rigidity desired.

The Steareth-2 and Isosteareth-20 are added to the hot liquid gel forming mixture and is mixed until clear. The Steareth-2 and Isosteareth-20, a straight chain fatty alcohol surfactant and a branched chain fatty alcohol surfactant, respectively, impart a stable clarity to the cosmetic stick of the present invention. While Isosteareth-20 alone will produce a stick that displays clarity for extended periods, a stick comprising a formulation that includes Isosteareth-20 and steareth-2 materials display a clarity that is maintained for periods of time in excess of 12 months and at temperatures as high as 45 degrees Centigrade.

The Isosteareth-20 is a PEG-20 Isostearyl ether, HLB-15.2. The steareth-2 is PEG-2 stearyl ether, HLB 4.9. In one embodiment, the Isosteareth-20 is manufactured by RTD Chem and the Steareth-2 is manufactured by Uniqema.

About 90% of the water is added to the clear mixture. Water and propylene glycol both act as solvents. When the water is added, the mixture is cooled to 70 degrees Centigrade, while mixing.

Sodium hydroxide solution is added to the mixture, with mixing. The color solution is then added to the mixture with mixing. The container that contained the color is rinsed with the remaining water. Fragrance is added to the mixture and mixed. The mixture is mixed at moderate speed and cooled to 65 degrees Centigrade in order to minimize volatization of the fragrance. The cooled mixture is poured into packages at a temperature of 60 to 65 degrees Centigrade. The packages containing the clear cosmetic are storable for at least about 12 months. The packages are storable and transportable at elevated temperatures.

The compositions of the present invention retain clarity in excess of twelve months following manufacture. The clarity is determined by observing the stick against light for the absence of any crystal or particulate matter. The clarity is also determined by viewing objects behind the clear stick, through the clear stick.

The clear cosmetic stick of the present invention includes, for some embodiments, cosmetically active materials other than or in addition to deodorant active materials. The cosmetically active materials include deodorant active materials, including fragrances and anti-bacterial agents, sunscreens, skin conditioners, nail conditioners, fungistats, ultraviolet absorbers, analgesics, anti-skin wrinkle agents, colorants, astringents, and antioxidants.

Presented herein are examples of specific formulations and clarity measured for these formulations. Concentrations are presented as percent by weight. These formulations are presented as examples only and are not intended to limit the scope of the present invention.

EXAMPLE 1

| Ingredient | Formulation 1 | Formulation 2 | Formulation 3 | Formulation 4 | Formulation 5 |
| --- | --- | --- | --- | --- | --- |
| Propyleneglycol | 70.69 | 67.91 | 70.39 | 70.43 | 70.13 |
| Deionized Water | 14.80 | 22.17 | 14.80 | 15.00 | 19.00 |
| Sodium Stearate | 6.50 | 6.50 | 6.50 | 6.50 | 9.00 |
| Isosteareth-20 | 5.00 | 1.50 | 5.00 | 5.00 | — |
| Steareth-2 | 1.00 | — | 1.00 | 1.00 | — |
| Triclosan | 0.25 | 0.25 | 0.25 | 0.25 | 0.25 |
| Vitamin E | 0.10 | 0.10 | — | — | — |
| 10% NaOH | 0.10 | — | 0.10 | 0.10 | — |
| Fragrance Oil | 1.50 | 1.50 | 1.70 | 1.50 | 1.50 |
| Allantoin | — | — | 0.10 | — | — |
| Menthol | — | — | 0.10 | — | — |
| Color Solution | QS | QS | QS | QS | QS |
| Clarity at Ambient Conditions | Clear 12+ months | Opaque 5 months | Clear 12+ months | Clear 7+ months | Opaque 2 months |

Formulation 1 in Example 1 is a deodorant formulation that includes both a branched chain fatty alcohol surfactant and a straight chain fatty alcohol surfactant.

Formulation 2 in Example 1 is a deodorant formulation that includes a branched chain fatty alcohol surfactant but doe not contain a straight chain fatty alcohol surfactant.

Formulations 3 and 4 are deodorants that include both a branched chain fatty alcohol surfactant and a straight-chain fatty alcohol surfactant.

Formulation 5 is a control formulation. The formulation is free of a branched chain fatty alcohol surfactant and a straight-chain fatty alcohol surfactant. The control formulation stability was about two months.

EXAMPLE 2

| Ingredient | Control Formulation | Formulation 6 |
| --- | --- | --- |
| Propylene glycol | 75.64 | 70.43 |
| Deionized Water | 15.80 | 15.01 |
| Sodium Stearate | 6.50 | 6.50 |
| Triclosan | 0.25 | 0.25 |
| Isosteareth-20 | 0.00 | 5.00 |
| Steareth-2 | 0.00 | 1.00 |
| 10% NaOH solution | 0.10 | 0.10 |
| Fragrance | 1.50 | 1.50 |
| Color solution | 0.22 | 0.22 |
| Total | 100.00 | 100.00 |

Two mixtures were prepared. The mixtures included a control mixture and a mixture for making Formulation 6. The propylene glycol is weighed and mixed with Triclosan to form each of the two mixtures. The mixtures were heated to 85 to 90 degrees Centigrade. The sodium stearate was added to the mixtures and dissolved into the mixtures. The Isosteareth-20 and Steareth-2 were added to the mixture for Formulation 6 and mixed well to dissolve. The Isosteareth-20 and Steareth-2 were not added to the Control mixture. Water was added to both of the mixtures. Both mixtures were cooled to 70 degrees Centigrade while mixing at low speed. Sodium hydroxide solution was added and mixed well into both mixtures. Fragrance was added to both mixtures. Color solutions were added to both mixtures. Both mixtures were mixed at a moderate speed while cooling at 65 degrees Centigrade. Both mixtures were poured into packages at 60 to 62 degrees Centigrade.

The clarity of each of the formulations was measured at prescribed intervals by observing the percent transmission at 600 nm. For one test, conducted over a twelve week period, products made with the Control Formulation and Formulation 6 were held at ambient temperature. Results for this test are illustrated graphically in FIG. 1. The results show a greater transmission for the product made with Formulation 6 than the product made with the Control formulation up to week 8. Week 12 also shows a greater transmission.

Figure 2:
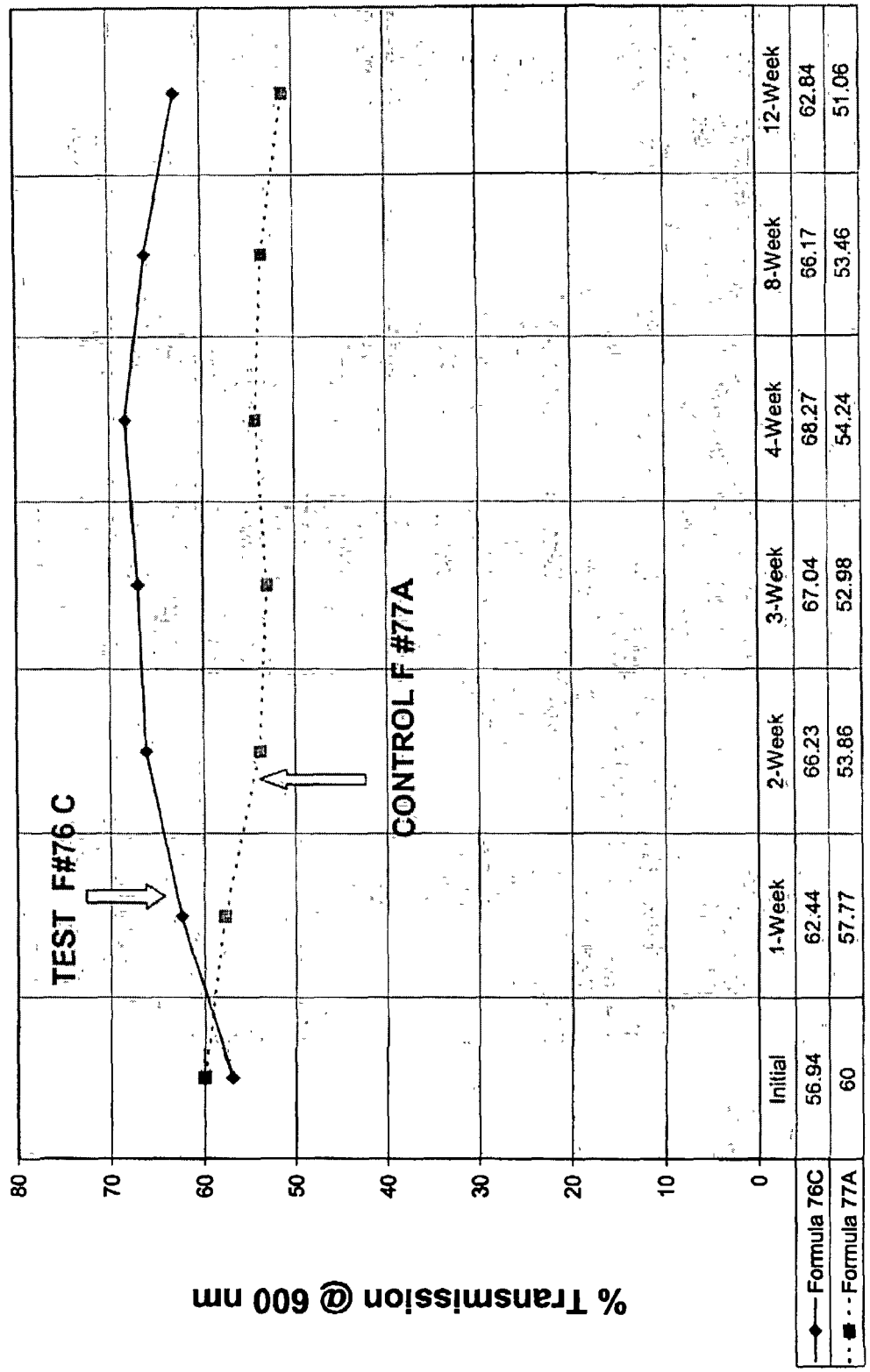
FIG. 2 is a graphical view of one embodiment of the clear cosmetic stick of the present invention and a second cosmetic stick outside of the present invention, stored at a temperature of 37 degrees Centigrade for 12 weeks.

The clarity of the formulations was measured over a 12 week period at 37 degrees Centigrade. The results are shown in FIG. 2. After the first week, the percent transmission of the product made with Formulation 6 was greater than the control transmission.

Figure 3:
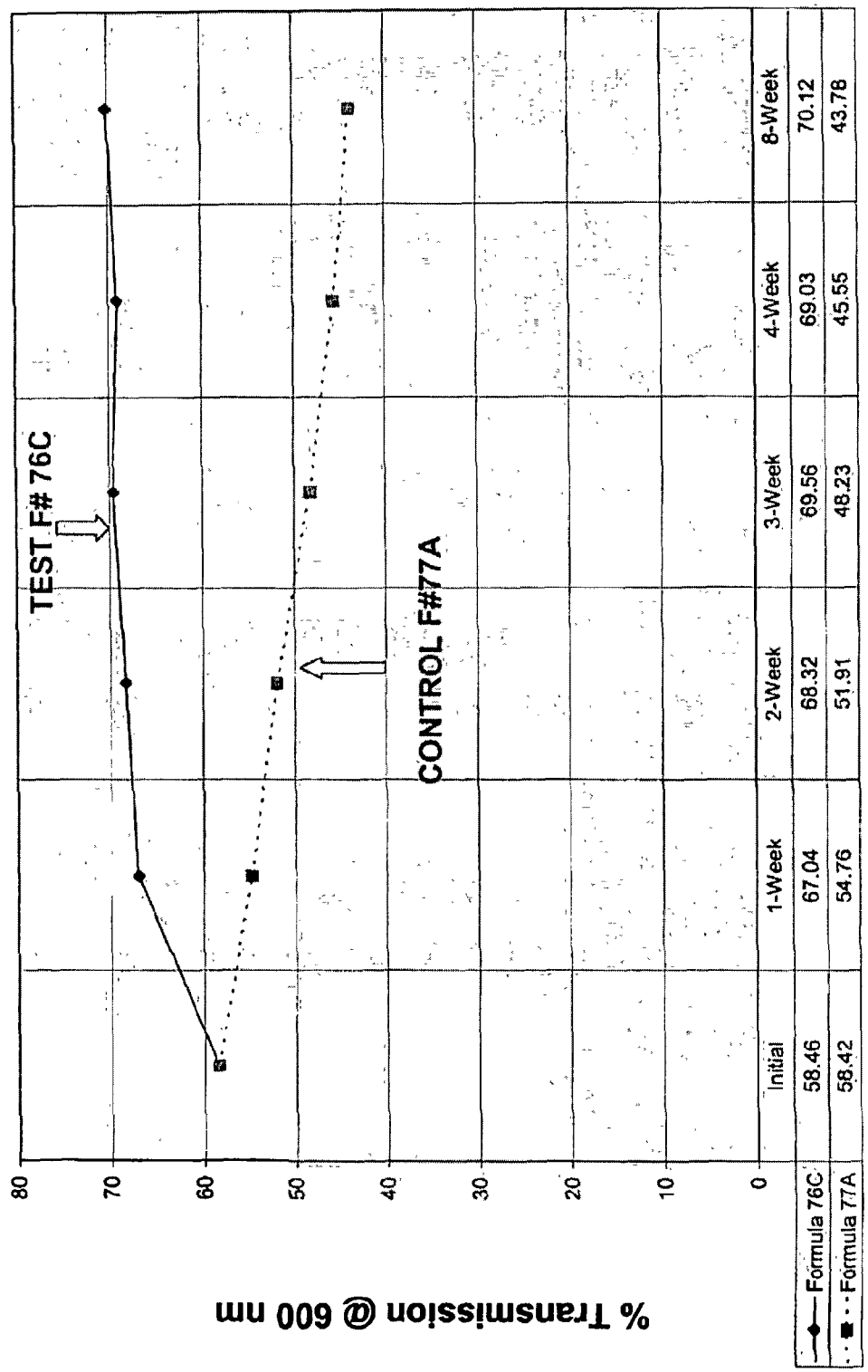
FIG. 3 is a graphical view of one embodiment of the clear cosmetic stick of the present invention and a second cosmetic stick outside of the present invention, stored at a temperature of 45 degrees Centigrade for 8 weeks.

The clarity of the formulations was measured over an 8 week period at 45 degrees Centigrade. The results are shown in FIG. 3. The transmission of the product made with Formulation 6 was greater than the control transmission over the course of the test. The magnitude of the difference increased over the 8 week period.

The clarity of the clear stick formulations of the present invention is stable when the clear sticks are exposed to temperature cycling. The term "temperature cycling" as used herein refers to a temperature change from ambient temperature to an elevated temperature as high as about 45 degrees Centigrade to a temperature back to ambient temperature.

Figure 4:
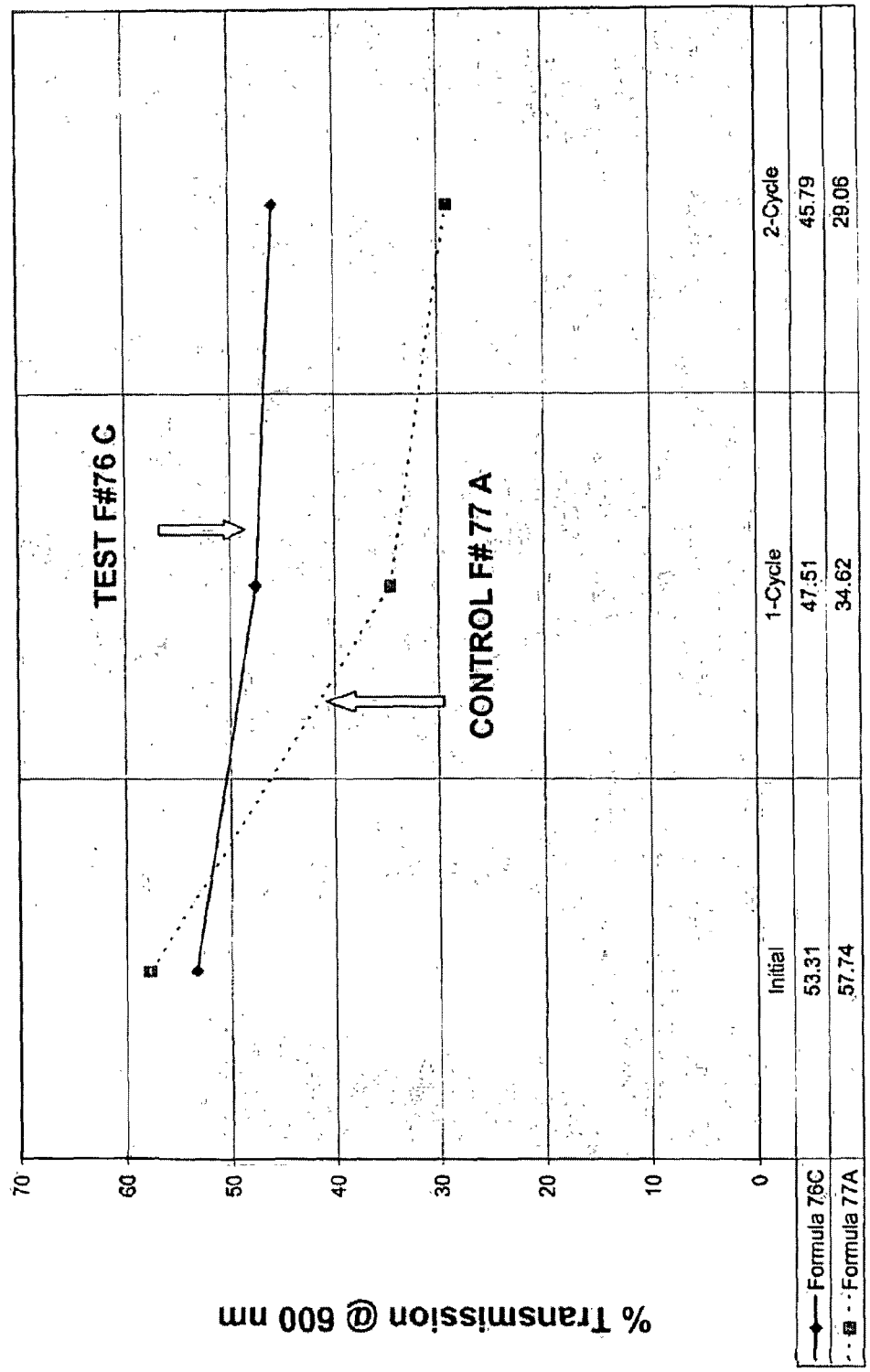
FIG. 4 is a graphical view of one embodiment of the clear cosmetic stick of the present invention and a second cosmetic stick outside of the present invention, subjected to temperature cycling.

In the test, the clear stick, made with formulation 6 and a stick made with the control formulation, are subjected to one temperature cycle of ambient temperature to 45 degrees Centigrade and back to ambient temperature. In the second part of the test, the clear stick, made with formulation 6 and a stick made with the control formulation, are raised to 45 degrees Centigrade and then returned to ambient temperature. The sticks are held at the cycle temperature for a minimum of 24 hours. Results of this test are shown graphically in FIG. 4. After the first temperature cycle, the clear stick made with formulation 6 had a percent transmission at 600 nanometers of 47.51 while the stick make with the control formulation had a percent transmission of 34.62. After the second temperature cycle, the clear stick made with formulation 6 had a clarity of 45.99, as measured as percent transmission at 600 nanometers. The clear stick made with the control formulation had a percent transmission at 600 nanometers of 29.06. Thus, the clear stick made with the formulation of the present invention was able to withstand multiple temperature cycling without significant loss of clarity.

EXAMPLE 3

Other embodiments of the present invention include cologne sticks and blush sticks. It has surprisingly been found that the cologne sticks have a fragrance concentration much higher than conventional fragrance sticks while retaining clarity for a period of months. In one embodiment, the fragrance oil is as high as 10.0% by volume. In another embodiment, blush sticks have been found to have a color concentration as high as 0.10% while retaining good visual clarity for a time period of at least one month.

The cologne stick formulations are as follows:

| Ingredient | Weight % in Embodiment 1 | Weight % in Embodiment 2 |
|---|---|---|
| Propylene Glycol | 72.10 | 63.60 |
| D.I Water | 10.30 | 12.30 |
| Sodium Stearate | 6.00 | 8.00 |
| Isosteareth-20 | 5.00 | 5.00 |
| Steareth-2 | 1.00 | 1.00 |
| 10% NaOH solution | 0.10 | 0.10 |
| Fragrance Oil | 5.50 | 10.00 |
| Color solution | QS | QS |

The blush stick formulations are as follows:

| Ingredient | Weight % in Embodiment 1 | Weight % in Embodiment 2 |
|---|---|---|
| Propylene Glycol | 61.25 | 66.25 |
| D.I. Water | 24.95 | 19.80 |
| Sodium Stearate | 6.50 | 6.50 |
| Isosteareth-20 | 5.00 | 5.00 |
| Steareth-2 | 1.00 | 1.00 |
| 10% NaOH Solution | 0.00 | 0.10 |
| Fragrance Oil | 1.00 | 1.00 |
| D&C Red No. 33 | 0.05 | 0.10 |

The blush sticks in embodiments 1 and 2 had good clarities for a time period of at least one month.

While the present invention is described in connection with specific embodiments, it is understood that it is not intended to limit the invention to the embodiments presented. To the contrary, it is intended to cover all alterations, modifications, and equivalents as may be included within the spirit and scope of the invention as defined by the appended claims.

What is claimed is:

1. A method for making a clear cosmetic stick, comprising:
providing a polyhydric alcohol and a deodorant active material and mixing the polyhydric alcohol with the deodorant active material together to form a deodorant active mixture;
adding a soap, gel forming agent to the deodorant mixture to form a gelled mixture; heating the mixture to 85 to 90 degrees Centigrade;
adding a clarity stabilization system to the gelled mixture to form a clarified mixture;
adding water to the mixture and cooling the mixture to 70 degrees Centigrade;
adding sodium hydroxide to the clarified mixture; and
pouring the clarified mixture into a container to form a clear cosmetic stick;
wherein the clarity stabilization system maintains clarity in the cosmetic stick when the cosmetic stick is exposed to a temperature range of 5 to 45 degrees Centigrade for a period of at least twelve months, and wherein the clarity stabilization system of the clear cosmetic stick consists essentially of a PEG-20 isostearyl ether having a hydrophile-lipophile blend of 15.2 and a PEG-2 stearyl ether having a hydrophile-lipophile blend of 4.9, wherein the concentration of the PEG-20 isostearyl ether in the cosmetic stick is in the range of 3 to 7 percent by weight of the cosmetic stick and the concentration of the PEG-2 stearyl ether in the cosmetic stick is in the range of 0.5 to 1.5 percent by weight of the cosmetic stick.

2. The method of claim 1 and further comprising adding one or more of a deodorant active material, a sunscreen, a skin conditioner, a nail conditioner, a fungistat, an ultraviolet absorber, an analgesic, an anti-wrinkle agent, an astringent and an antioxidant.

3. The method of claim 1 wherein the clarity stabilization system of the clear cosmetic stick consists of the PEG-20 isostearyl ether having a hydrophile-lipophile blend of 15.2 and the PEG-2 stearyl ether having a hydrophile-lipophile blend of 4.9.

4. The method of claim 1 further comprising adding a fragrance, wherein the fragrance makes up to 10% of the volume of the cosmetic stick.

5. The method of claim 4 wherein the fragrance makes up 10% of the weight of the cosmetic stick.

6. The method of claim 4 wherein the fragrance makes up 0.1% to 5% of the weight of the cosmetic stick.

7. The method of claim 1 further comprising adding a coloring agent, wherein the coloring agent makes up to 0.1% of the weight of the cosmetic stick.

8. The method of claim 7 wherein the coloring agent makes up 0.1% of the weight of the cosmetic stick.

* * * * *